(12) United States Patent
Hansted et al.

(10) Patent No.: US 8,586,079 B2
(45) Date of Patent: Nov. 19, 2013

(54) PROMOTIONAL SIMULATION FOR TRANSDERMAL PATCH SAMPLER

(75) Inventors: Kenneth W. Hansted, New York, NY (US); David Sanders, Brooklyn, NY (US); Philip Welsher, Hillsborough, NJ (US)

(73) Assignee: Graphic Productions Inc., New York, NY (US)

( * ) Notice: Subject to any disclaimer, the term of this patent is extended or adjusted under 35 U.S.C. 154(b) by 2105 days.

(21) Appl. No.: 10/176,517

(22) Filed: Jun. 21, 2002

(65) Prior Publication Data

US 2003/0235608 A1 Dec. 25, 2003

(51) Int. Cl.
- A61F 13/00 (2006.01)
- A61F 13/02 (2006.01)
- A61K 9/70 (2006.01)
- A61L 15/16 (2006.01)

(52) U.S. Cl.
USPC ............................ 424/449; 424/448; 424/443

(58) Field of Classification Search
USPC ...................... 424/449, 448, 443; 132/79, 319
See application file for complete search history.

(56) References Cited

U.S. PATENT DOCUMENTS

| | | | |
|---|---|---|---|
| 5,161,688 A * | 11/1992 | Muchin ........................ | 206/484 |
| 5,391,420 A | 2/1995 | Bootman et al. | |
| 5,904,930 A | 5/1999 | Fischer et al. | |

FOREIGN PATENT DOCUMENTS

FR 2611965 9/1988

* cited by examiner

Primary Examiner — Isis Ghali
(74) Attorney, Agent, or Firm — Gary J. Gershik; Cooper & Dunham LLP

(57) ABSTRACT

A promotional insert for advertising a transdermal patch to a reader of a periodical comprising a sample of the transdermal patch attached to the promotional insert, wherein the promotional insert contains a description of the sample of the transdermal patch attached thereto, and wherein the promotional insert is suitable for inclusion into a periodical. A process for producing the promotional insert, and a use of the promotional insert in a magazine for advertisement of the transdermal patch are also described.

31 Claims, 2 Drawing Sheets

PROMOTIONAL SIMULATION FOR TRANSDERMAL PATCH SAMPLER

Throughout this application, the disclosures of publications referenced are hereby incorporated by reference in their entireties into this application in order to more fully describe the state of the art as known to those skilled therein as of the date of the invention described and claimed herein.

BACKGROUND OF THE INVENTION

A transdermal patch is often used for percutaneous delivery of a pharmaceutical substance, i.e. drug delivery. The methodology and design of transdermal patches for delivery of pharmaceutical substances are well known in the pharmaceutical art. A. R. Gennaro, Ed., *Remington: The Science and Practice of Pharmacy*, 20$^{th}$ ed., Lippincott, Williams & Wilkins (2000). Continuing improvements are being made by the pharmaceutical industry with respect to the formulations that permit percutaneous delivery of substances. More and more substances are being formulated for use in transdermal patches. In addition, improvements are also being made to the transdermal patch in terms of the formulations it can deliver, its appearance and its feel on the skin of a person. Thus, there is a need in the pharmaceutical industry for effective advertisement of transdermal patches.

Previous print and broadcast advertising for transdermal patches has relied on photographic imagery or verbal descriptions of the patch product. In some advertising a toll free number or address was given to allow a potential user to request more details, but no ability existed to allow the user a tactile experience.

Since the transdermal patch is applied to the skin and worn for extended periods of time, both the look and feel of the product are essential to creating a perception of practicality in the users mind.

It was not possible to accomplish the goal of sampling the production to likely users with previous advertising since no cost effective method existed to deliver a simulation of the transdermal product in a wide distribution advertising campaign.

SUMMARY OF THE INVENTION

This invention provides a promotional insert for advertising a transdermal patch to a reader of a periodical comprising
a sample of the transdermal patch attached to the promotional insert,
wherein the promotional insert contains a description of the sample of the transdermal patch attached thereto, and wherein the promotional insert is suitable for inclusion into a periodical.

This invention also provides a process of producing the promotional insert comprising
forming a sample of the transdermal patch on a release liner,
removing the sample of the transdermal patch from the release liner, and
affixing the sample of the transdermal patch onto a preprinted insert suitable for periodical use, wherein the preprinted insert contains a description of the sample of the transdermal patch being affixed thereto,
thereby producing the promotional insert.

This invention also provides a method of advertising a transdermal patch to a reader of a periodical comprising disseminating a periodical comprising the promotional insert described above, thereby advertising the transdermal patch.

DETAILED DESCRIPTION OF THE INVENTION

Figure 1:
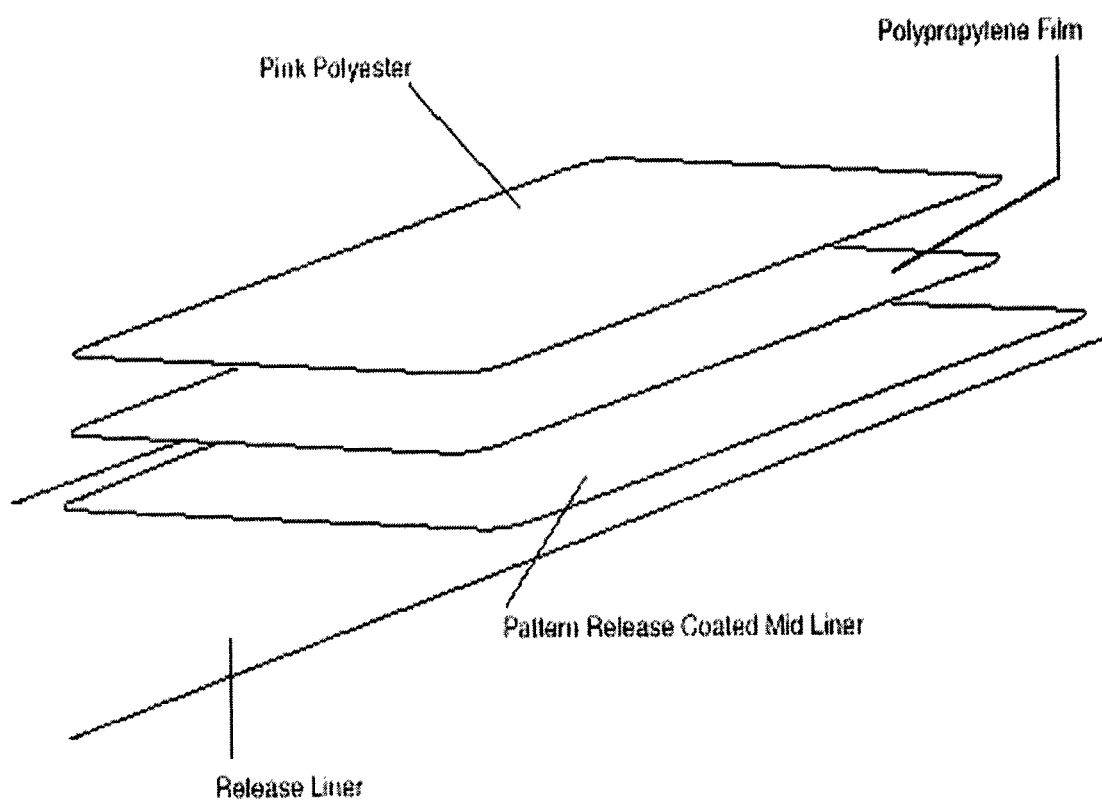
FIG. 1 is a diagram view of the construction of a rectangular promotional patch sampler with rounded corner laminated to an intermediate liner that will allow for partial "peel up" of the patch and a carrier (release liner). The construction of the patch is suited for automated, high speed, application to carrier.

This invention provides a promotional insert for advertising a transdermal patch to a reader of a periodical comprising
a sample of the transdermal patch attached to the promotional insert,
wherein the promotional insert contains a description of the sample of the transdermal patch attached thereto, and wherein the promotional insert is suitable for inclusion into a periodical.

In the promotional insert, the sample of the transdermal patch may be similar to the sense of touch of the reader to the transdermal patch, or may be substantially identical to the sense of touch of the reader to the transdermal patch.

The sample of the transdermal patch may be similar in color to the transdermal patch, or the sample of the transdermal patch may be substantially identical in color to the transdermal patch. The sample of the transdermal patch may be skin colored.

In the promotional insert, the sample of the transdermal patch may contain a placebo. Alternatively, the sample of the transdermal patch may contains an active preparation that is identical to the active preparation of the transdermal patch.

The periodical may be a magazine.

The promotional insert may be attached, e.g. bound, to the periodical or simply inserted into the periodical.

The sample of the transdermal patch may be removable from the insert and affixable to skin.

In an embodiment, the sample of the transdermal patch is attached to the insert by a first adhesive at a first portion, and by a second adhesive at a second portion, wherein the first adhesive is permanent and the second adhesive is resealable. In another embodiment, the sample of the transdermal patch is attached to the insert by a pattern release coat under a portion of the patch, where only the portion attached by the pattern release coat is removable.

In the promotional insert, wherein the sample of the transdermal patch may comprise a polyester layer laminated with a polypropylene layer, and an adhesive suitable for skin adhesion on the polypropylene layer.

The promotional insert may further comprise a coupon for the purchase of the transdermal patch.

In an embodiment, the sample of the transdermal patch may be made of a facing layer, a bulking layer underneath the facing layer and onto which the adhesive is applied.

The facing layer can be a polymeric base, in the case of 3M Scotchpak 9723, a clear polyester film with an extruded polyethylene coating creating a translucent flesh toned matte appearance on one side. Color may vary based on the needs of the product to be simulated. Examples of facing layers are 3M Scotchpak 9723, Mylan Technologies Mediflex 1501, or similar product.

The bulking layer can be polypropylene, polyvinyl or spun bond/non-woven fibers (such as those produced by Snow Filtration or Ahlstrom). This layer will vary to best accommodate the look and feel of the transdermal that is to be simulated. In an embodiment of the invention, the bulking layer is nominal 2 mil. polypropylene, which attains the bulk and flexibility of the transdermal product.

The adhesive may be a skin contact adhesive. The skin contact adhesive should comply with the Code of Federal Regulations for skin contact, see 29 C.F.R. §1910. An example of a suitable skin contact adhesive is Primamelt 28-75-1. This layer will vary to best accommodate the look and feel of the transdermal patch that is to be simulated. In an embodiment of the invention, the skin contact adhesive is Primamelt 28-75-1, which is a non-clear, amber colored, adhesive that was used to help attain the proper product color and translucency.

This invention also provides a process of producing the promotional insert comprising
  forming a sample of the transdermal patch on a release liner,
  removing the sample of the transdermal patch from the release liner, and
  affixing the sample of the transdermal patch onto a preprinted insert suitable for periodical use, wherein the preprinted insert contains a description of the sample of the transdermal patch being affixed thereto,
  thereby producing the promotional insert.

The release liner, also called "pattern release", is printed with a pattern silicone based release coating, if partial release only is required. A release deadener may also be used. The release liner layer is interchangeable with any stock that will accept the pattern release coating with the proper ink/silicone hold out for functionality or with standard release liners if partial release only is not required. Some possible alternatives include polypropylene or polyester, standard kraft liner or any coated stock.

This release liner layer maybe adapted for use as the carrier layer in which case the pattern release coat would not be printed on the liner, but maybe printed on the final piece that the label will be affixed to, or pattern adhesives may be printed, to simulate the same effect. In an embodiment of this invention, 60# white semi-gloss is used.

The underside of the release liner may be coated with an adhesive for the creation of a "piggyback" style label.

This invention also provides a periodical comprising the promotional insert described above. The periodical may be a magazine.

This invention also provides a method of advertising a transdermal patch to a reader of a periodical comprising disseminating a periodical comprising the promotional insert described above, thereby advertising the transdermal patch.

Thus, disclosed is a method of advertising a transdermal patch to a reader of a periodical comprising
  including in the periodical a sample of the transdermal patch
  wherein the sample of the transdermal patch is available for the reader to touch, thereby advertising the transdermal patch to the reader of the periodical.

In the method, the sample of the transdermal patch may be similar to the sense of touch of the reader as the transdermal patch, or the sample of the transdermal patch may be substantially identical to the sense of touch of the reader as the transdermal patch.

In the method, the sample of the transdermal patch may be similar in color to the transdermal patch, or the sample of the transdermal patch may be substantially identical in color to the transdermal patch. The sample of the transdermal patch may be skin colored.

In the method, the sample of the transdermal patch may contain a placebo. Alternatively, the transdermal patch may contain an active preparation that is identical to the active preparation of the transdermal patch.

In the method, the periodical may be is a magazine.

In the method, the sample of the transdermal patch may be attached to the periodical. The sample of the transdermal patch may also be attached to a promotional insert in the periodical. In the method the sample of the transdermal patch is attached to a promotional insert which may be bound into the periodical.

In the method, the sample of the transdermal patch may be removable from the periodical and affixable to skin.

In the method, the sample of the transdermal patch may be attached to a promotional insert by a first adhesive at a first portion, and by a second adhesive at a second portion, wherein the first adhesive is permanent and the second adhesive is resealable. Alternatively, the sample of the transdermal patch may be attached to a promotional insert by a pattern release coat under a portion of the patch, where only the portion attached by the pattern release coat is removable.

The foregoing embodiments of the subject invention may be accomplished according to the guidance which follows. Certain of the foregoing embodiments are exemplified. Sufficient guidance is provided for a skilled artisan to arrive at all of the embodied aspects of the subject invention.

EXAMPLE 1

Promotional Transdermal Patch Sample.

A simulation of a transdermal patch for non-clinical promotional use was produced. The patch layer was comprised of polymeric laminates, the face showing laminate being a matte finished, translucent flesh-tone polyethylene laminated to a polyester such that there will be a matte and a glossy side to the flesh-tone layer (identical to 3M Scotchpak 9723™ or Mylan Technologies Mediflex 1501™). This polymeric laminate was then laminated to a polypropylene layer so as to provide bulk and flexibility, and to create the look and feel of the pharmaceutically dispensed transdermal patch. The simulated patch was then die cut and provided onto a carrier (release liner) useful for automated application or is further laminated onto an intermediate layer (mid liner) which will be die cut and then provided onto a carrier (release liner) useful for automated application to a promotional insert. The intermediate layer (mid liner) may be coated or pattern coated to allow total or partial removal of the simulated patch from the intermediate layer. Also, the intermediate layer may be coated or pattern coated to allow for the entire patch or only a portion of the patch to have adhesive if the patch is removed in total from the intermediate layer.

Figure 2:
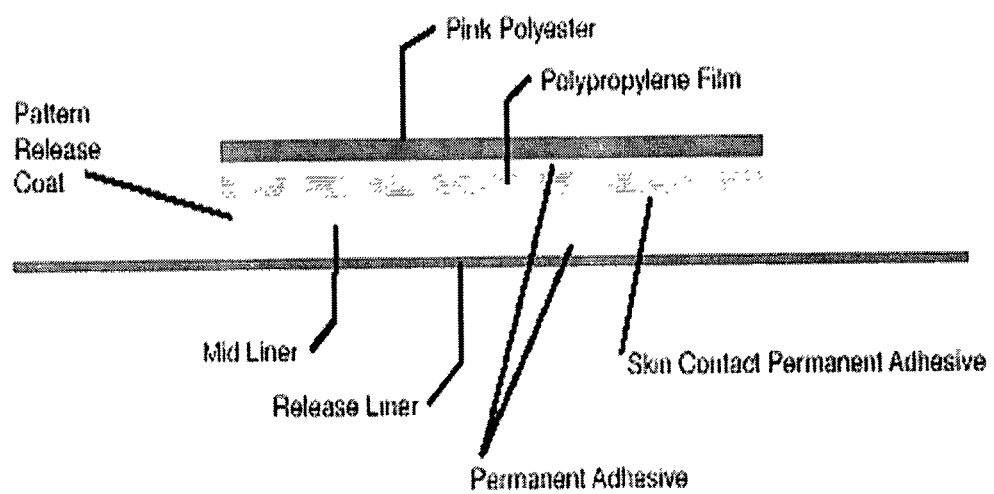
FIG. 2 is a transverse section through the promotional patch sampler of FIG. 1.

To aid understanding of the invention, it is described with respect to an example thereof shown in the accompanying drawings. Specifically, FIGS. 1 and 2 show a transdermal patch sampler having 1) a top ply 1-13/16 with radial corners as in the pharmaceutically dispensed product constructed of 1.7 mil 3M™ Pink Polyester adhesive laminated permanently to a nominal 2 mm polypropylene film layer; 2) a permanent skin contact approved adhesive; 3) a nominal 2 inch outer diameter of extended pattern release mid-liner; 4) a permanent adhesive; and 5) a standard release liner (carrier roll, 3 inch cores).

Construction Specifications

Description: Promotional Magazine Bind-In Insert consisting of a printed card with a simulation of the transdermal patch affixed to it.

Bind-In Card: 4-1/4×6-3/4 in, perfect bound version or 4-1/4× 10-1/2 in, saddle stitch version printed on a 100# Productolith™ gloss coated text.

Patch/Label: A beige colored flexible film (3M product #9723 Scotchpak™) matching the desired standard reference spectrum (i.e. matching the transdermal patch), in a multiply lamination with a polypropylene and a pattern release coated white paper carrier. The beige top layer is die cut to the desired specification (i.e. to the characteristic of the transdermal patch being advertised.) The simulation of the transdermal patch was made of a beige colored laminate with a bright shiny layer (polyester layer) and a dull matte layer (polyethylene layer). 3M product #9723 Scotchpak™ polyester film laminate, and tan semi-translucent polyethylene were used. This resulted in a beige colored, flexible film laminate with a bright shiny side and a dull matte side free of visible contaminants. The white pattern coated carrier extended approximately one eight inch beyond the beige layer.

Affixing: The simulated transdermal patch was affixed to the bind-in per the creative specifications from of the advertisement.

Packing: The Promotional Magazine Bind-In Inserts were carton packed. On edge packing was required in this example due to the nonstandard and nonuniform thickness of the insert to avoid curling. Turning in lifts was also required due to the nonstandard thickness. All turns were separated with a divider and turns were kept to a minimum for best efficiency at the point of assembly of the periodicals.

This rendition has been approved by the U.S. Postal Office for use in magazine insertion under magazine rates. This means that no additional postage fees will be charged because it has been classified as only a rendition as opposed to a real sample of the pharmaceutically dispensed product.

What is claimed is:

1. A promotional insert for advertising a transdermal patch to a reader of a periodical comprising
a sample of the transdermal patch attached to the promotional insert,
wherein the promotional insert contains a description of the sample of the transdermal patch attached thereto, wherein the promotional insert is suitable for inclusion into a periodical, and
wherein the sample of the transdermal patch is
attached to the insert by a first adhesive at a first portion. and by a second adhesive at a second portion, wherein the first adhesive is permanent and the second adhesive is resealable;
attached to the insert by a pattern release coat under a portion of the patch, where only the portion attached by the pattern release coat is removable, or
removable from the insert and affixable to the skin.

2. The promotional insert of claim 1, wherein the sample of the transdermal patch is similar to the sense of touch of the reader to the transdermal patch.

3. The promotional insert of claim 1, wherein the sample of the transdermal patch is substantially identical to the sense of touch of the reader to the transdermal patch.

4. The promotional insert of claim 1, wherein the sample of the transdermal patch is similar in color to the transdermal patch.

5. The promotional insert of claim 1, wherein the sample of the transdermal patch is substantially identical in color to the transdermal patch.

6. The promotional insert of claim 1, wherein the sample of the transdermal patch is skin colored.

7. The promotional insert of claim 1, wherein the sample of the transdermal patch contains a placebo.

8. The promotional insert of claim 1, wherein the sample of the transdermal patch contains an active preparation that is identical to the active preparation of the transdermal patch.

9. The promotional insert of claim 1, wherein the periodical is a magazine.

10. The promotional insert of claim 1, wherein the promotional insert is attached to the periodical.

11. The promotional insert of claim 1, wherein the sample of the transdermal patch comprises a polyester layer laminated with a polypropylene layer, and an adhesive suitable for skin adhesion on the polypropylene layer.

12. The promotional insert of claim 1, further comprising a coupon for the purchase of the transdermal patch.

13. A process of producing the promotional insert of claim 1 comprising
forming a sample of the transdermal patch on a release liner,
removing the sample of the transdermal patch from the release liner, and
affixing the sample of the transdermal patch onto a pre-printed insert suitable for periodical use, wherein the preprinted insert contains a description of the sample of the transdermal patch being affixed thereto,
thereby producing the promotional insert.

14. A periodical comprising the promotional insert of claim 1.

15. The periodical of claim 14, wherein the periodical is a magazine.

16. A method of advertising a transdermal patch to a reader of a periodical comprising disseminating the periodical of claim 14, thereby advertising the transdermal patch.

17. A method of advertising a transdermal patch to a reader of a periodical comprising
including in the periodical the promotional insert of claim 1 including the transdermal patch
wherein the sample of the transdermal patch is available for the reader to touch, thereby advertising the transdermal patch to the reader of the periodical.

18. The method of claim 17, wherein the sample of the transdermal patch is similar to the sense of touch of the reader as the transdermal patch.

19. The method of claim 17, wherein the sample of the transdermal patch is substantially identical to the sense of touch of the reader as the transdermal patch.

20. The method of claim 17, wherein the sample of the transdermal patch is similar in color to the transdermal patch.

21. The method of claim 17, wherein the sample of the transdermal patch is substantially identical in color to the transdermal patch.

22. The method of claim 17, wherein the sample of the transdermal patch is skin colored.

23. The method of claim 17, wherein the sample of the transdermal patch contains a placebo.

24. The method of claim 17, wherein the sample of the transdermal patch contains an active preparation that is identical to the active preparation of the transdermal patch.

25. The method of claim 17, wherein the periodical is a magazine.

26. The method of claim 17, wherein the sample of the transdermal patch is attached to the periodical.

27. The method of claim 17, wherein the sample of the transdermal patch is attached to a promotional insert in the periodical.

28. The method of claim 27, wherein the sample of the transdermal patch is attached to a promotional insert which is bound into the periodical.

29. The method of claim 26, wherein the sample of the transdermal patch is removable from the periodical and affixable to skin.

30. The method of claim 27, wherein the sample of the transdermal patch is attached to a promotional insert by a first adhesive at a first portion, and by a second adhesive at a second portion, wherein the first adhesive is permanent and the second adhesive is resealable.

31. The method of claim 27, wherein the sample of the transdermal patch is attached to a promotional insert by a pattern release coat under a portion of the patch, where only the portion attached by the pattern release coat is removable.

* * * * *